United States Patent
Finnestad et al.

(10) Patent No.: US 12,177,989 B2
(45) Date of Patent: Dec. 24, 2024

(54) DIRECT WIRE ATTACHMENT METHODS AND APPARATUS FOR A BGA COMPONENT

(71) Applicant: ATL Technology, LLC, Springville, UT (US)

(72) Inventors: Donovan M. Finnestad, Clackamas, OR (US); Bradford James Brown, Highland, UT (US); John Carl Holloway, Fort Myers, FL (US)

(73) Assignee: ATL TECHNOLOGY, LLC, Springville, UT (US)

( * ) Notice: Subject to any disclaimer, the term of this patent is extended or adjusted under 35 U.S.C. 154(b) by 231 days.

(21) Appl. No.: 17/988,459

(22) Filed: Nov. 16, 2022

(65) Prior Publication Data

US 2023/0156927 A1 May 18, 2023

Related U.S. Application Data (60) Provisional application No. 63/279,765, filed on Nov. 16, 2021.

(51) Int. Cl.
 *H05K 3/34* (2006.01)
(52) U.S. Cl.
 CPC . *H05K 3/3436* (2013.01); *H05K 2201/10734* (2013.01)
(58) Field of Classification Search
 CPC .................. H05K 3/3436; H05K 2201/10734
 USPC ......................................................... 174/260
 See application file for complete search history.

(56) References Cited

U.S. PATENT DOCUMENTS

| 4,769,906 A | 9/1988 | Purpura et al. |
| 5,281,762 A | 1/1994 | Long et al. |
| 6,585,528 B1* | 7/2003 | Lin .................... H01R 13/6658 |
| | | 439/942 |
| 8,292,655 B1 | 10/2012 | Ling et al. |
| 10,403,418 B2 | 9/2019 | Aoyagi et al. |
| 10,510,918 B2 | 12/2019 | Hu et al. |
| 2012/0252266 A1* | 10/2012 | Ling ...................... H01R 12/62 |
| | | 29/832 |
| 2018/0219310 A1 | 8/2018 | Lukofsky et al. |

FOREIGN PATENT DOCUMENTS

| JP | 2008181817 | 8/2008 |
| JP | 2009170142 | 7/2009 |
| JP | 5871217 | 3/2016 |
| JP | 5962275 | 8/2016 |
| KR | 101318543 | 10/2013 |
| WO | 2009139041 | 11/2009 |

\* cited by examiner

*Primary Examiner* — Andargie M Aychillhum
(74) *Attorney, Agent, or Firm* — Kunzler Bean & Adamson (57) ABSTRACT

An electrical device that includes a ball grid array (BGA) component, comprising signal processing circuitry, a component mounting surface, and a BGA, which has solder balls that are spaced apart from each other on the component mounting surface. The electrical device also includes a plurality of electrical wires, each electrically coupled directly to a corresponding one of the solder balls of the BGA component. The electrical device further includes a wire fixation element, through which the plurality of electrical wires at least partially pass through. The wire fixation element is coupled to the plurality of electrical wires and configured to fix the electrical wires relative to each other so that the electrical wires do not move relative to each other.

20 Claims, 9 Drawing Sheets

DIRECT WIRE ATTACHMENT METHODS AND APPARATUS FOR A BGA COMPONENT

CROSS-REFERENCE TO RELATED APPLICATION

This application claims the benefit of U.S. Provisional Patent Application No. 63/279,765, filed Nov. 16, 2021, which is incorporated by reference in its entirety.

FIELD

This disclosure relates generally to electrical devices, and more particularly to electrically coupling a ball-grid array (BGA) of an electrical component directly to electrical wires.

BACKGROUND

Many electrical devices include electrical components mounted to a printed circuit board. The printed circuit board facilitates an electrical connection between the electrical components and electrical power and/or data communication elements, such as wires and cables. In other words, the printed circuit board operates as an interface between the electrical components and the electrical communication elements. The printed circuit board commonly employs mounting pads, which are configured to conduct electrical signals.

Electrical components having a ball-grid array ("BGA") of solder balls can be mounted to the mounting pads using Surface Mount Technology ("SMT") techniques. Typical SMT techniques involve mounting electrical components onto a major surface (e.g., broad surface) of the printed circuit board. While conventional SMT techniques are appropriate for some electrical devices, for other electrical devices, such as those that demand a streamlined profile, conventional SMT techniques are inadequate. Moreover, some alternative methods for mounting electrical components with a BGA of solder balls to a printed circuit board to accommodate a streamline profile have shortcomings. However, electrically connecting an electrical component with a BGA of solder balls to electrical power and/or data communication elements in a reliable and durable manner, without the use of a printed circuit board, can be difficult.

SUMMARY

The subject matter of the present application has been developed in response to the present state of the art, and in particular, in response to the shortcomings of conventional SMT techniques for mounting electrical components in certain applications, such as those that require a streamlined or compact design, that have not yet been fully solved by currently available techniques. Accordingly, the subject matter of the present application has been developed to provide a stable and robust electrical connection from the BGA of an electrical device directly to electrical wires, without using a printed circuit board, that overcomes many of the above-discussed shortcomings of prior art techniques.

Disclosed herein is an electrical device that comprises a ball grid array (BGA) component, comprising signal processing circuitry, having a component mounting surface, and a BGA, having solder balls that are spaced apart from each other on the component mounting surface. The electrical device also comprises a plurality of electrical wires, each electrically coupled directly to a corresponding one of the solder balls of the BGA component. The electrical device further comprises a wire fixation element, through which the plurality of electrical wires at least partially pass through. The wire fixation element is coupled to the plurality of electrical wires and configured to fix the electrical wires relative to each other so that the electrical wires do not move relative to each other. The preceding subject matter of this paragraph characterizes example 1 of the present disclosure.

The plurality of electrical wires extend perpendicularly relative to the component mounting surface of the BGA component. The preceding subject matter of this paragraph characterizes example 2 of the present disclosure, wherein example 2 also includes the subject matter according to example 1, above.

The plurality of electrical wires comprise coaxial wires each comprising a center conductor, a dielectric layer encircling the center conductor, and a ground layer encircling the dielectric layer. Each one of the coaxial wires passes entirely through the wire fixation element. The preceding subject matter of this paragraph characterizes example 3 of the present disclosure, wherein example 3 also includes the subject matter according to example 2, above.

The plurality of electrical wires further comprises a wire slug. The wire slug is electrically coupled directly to a grounding one of the solder balls of the BGA component. The preceding subject matter of this paragraph characterizes example 4 of the present disclosure, wherein example 4 also includes the subject matter according to example 3, above.

The wire slug only partially passes through the wire fixation element. The wire fixation element comprises an electrically-conductive bridge in contact with and electrically coupling together the ground layers of the coaxial wires and the wire slug. The preceding subject matter of this paragraph characterizes example 5 of the present disclosure, wherein example 5 also includes the subject matter according to example 4, above.

The wire fixation element further comprises a non-conductive material that surrounds and envelopes at least a portion of the component mounting surface, an entirety of the wire slug, an entirety of the electrically-conductive bridge, an entirety of the coaxial wires between component mounting surface and the electrically-conductive bridge, and at least a portion of the coaxial wires extending out of the electrically-conductive bridge away from the component mounting surface. The preceding subject matter of this paragraph characterizes example 6 of the present disclosure, wherein example 6 also includes the subject matter according to example 5, above.

The wire fixation element comprises a wire guide, which abuts the component mounting surface and comprises a plurality of channels. The plurality of wire channels are spaced apart from each other. Each one of the coaxial wires and the wire slug passes entirely through a corresponding one of the plurality of wire channels. The preceding subject matter of this paragraph characterizes example 7 of the present disclosure, wherein example 7 also includes the subject matter according to any of examples 4-6, above.

The wire guide comprises a body and at least one electrically insulating wall extending from the body. The body comprises the plurality of wire channels. The at least one electrically insulating wall defines open channels isolated from each other by the at least one electrically insulating wall. The at least one electrically insulating wall abuts the component mounting surface of the BGA component. Each one of the coaxial wires and the wire slug occupies a corresponding one of the open channels defined by the at least one electrically insulating wall. The preceding subject matter of this paragraph characterizes example 8 of the present disclosure, wherein example 8 also includes the subject matter according to example 7 above.

Each one of the plurality of wire channels, through which coaxial wires pass, comprises a first section and a second section. The first section has a diameter substantially equal to a diameter of the dielectric layer so that the dielectric layer forms a transition fit with the first section. The second section has a diameter substantially equal to a diameter of the center conductor so that the center conductor forms a transition fit with the second section. The diameter of the first section is greater than the diameter of the second section. The preceding subject matter of this paragraph characterizes example 9 of the present disclosure, wherein example 9 also includes the subject matter according to any of examples 7-8, above.

The wire channel, through which the wire slug passes, has a diameter greater than the diameter of the first section. The preceding subject matter of this paragraph characterizes example 10 of the present disclosure, wherein example 10 also includes the subject matter according to example 9 above.

The wire fixation element further comprises an electrically-conductive bridge in contact with and electrically coupling together the ground layers of the coaxial wires and the wire slug. The wire guide is interposed between the component mounting surface and the electrically-conductive bridge. The preceding subject matter of this paragraph characterizes example 11 of the present disclosure, wherein example 11 also includes the subject matter according to any of examples 8-10, above.

The electrically-conductive bridge comprises a solder blob. The preceding subject matter of this paragraph characterizes example 12 of the present disclosure, wherein example 12 also includes the subject matter according to example 11, above.

The electrical device a further comprises a tip assembly, comprising a tip housing and the wire guide. The tip housing comprises a receptacle that houses the BGA component. The tip housing and the wire guide form a one-piece monolithic and seamless construction. The preceding subject matter of this paragraph characterizes example 13 of the present disclosure, wherein example 13 also includes the subject matter according to any of examples 7-12, above.

An outermost periphery of the wire guide, defined relative to a plane that is parallel to the component mounting surface, is not larger than an outermost periphery of the BGA component, defined relative to the plane. The preceding subject matter of this paragraph characterizes example 14 of the present disclosure, wherein example 14 also includes the subject matter according to any of examples 7-13, above.

Further disclosed herein is an endoscope. The endoscope comprises an image sensor, comprising a component mounting surface and a ball grid array (BGA), having solder balls spaced apart from each other, on the component mounting surface. The endoscope also comprises a plurality of coaxial wires, each electrically coupled directly to a corresponding one of the solder balls of the image sensor and each extending perpendicularly relative to the component mounting surface of the image sensor. The endoscope further comprises a wire fixation element, through which the plurality of coaxial wires entirely pass through. The wire fixation element is coupled to the plurality of coaxial wires and configured to fix the coaxial wires relative to each other so that the coaxial wires do not move relative to each other. The preceding subject matter of this paragraph characterizes example 15 of the present disclosure.

An outermost periphery of the wire fixation element, defined relative to a plane that is parallel to the component mounting surface, is not larger than an outermost periphery of the image sensor, defined relative to the plane. The preceding subject matter of this paragraph characterizes example 16 of the present disclosure, wherein example 16 also includes the subject matter according to example 15, above.

Each one of the coaxial wires comprises a center conductor, a dielectric layer encircling the center conductor, and a ground layer encircling the dielectric layer. The endoscope further comprises a wire slug electrically coupled directly to a grounding one of the solder balls of the image sensor and extending perpendicularly relative to the component mounting surface of the image sensor. The wire fixation element comprises at least one of an electrically-conductive bridge in contact with and electrically coupling together the ground layers of the coaxial wires and the wire slug, or a wire guide, which abuts the component mounting surface and comprises a plurality of channels. The plurality of wire channels are spaced apart from each other. Each one of the coaxial wires and the wire slug passes entirely through a corresponding one of the plurality of wire channels. The preceding subject matter of this paragraph characterizes example 17 of the present disclosure, wherein example 17 also includes the subject matter according to any of examples 15-16, above.

Additionally disclosed herein is a method of making an electrical device. The method comprises positioning a plurality of electrical wires such that an electrical conductor of each one of the plurality of electrical wires is perpendicular to a component mounting surface of a ball grid array (BGA) component. The method also comprises soldering the electrical conductor of each one of the plurality of electrical wires, when positioned perpendicular to the component mounting surface of the BGA component, to a corresponding one of a plurality of solder balls of a BGA formed on the component mounting surface of the BGA component. The method additional comprises fixing together the plurality of electrical wires at a location away from the component mounting surface so that the plurality of electrical wires do not move relative to each other. The preceding subject matter of this paragraph characterizes example 18 of the present disclosure.

Fixing together the plurality of electrical wires comprises abutting a wire guide against the component mounting surface of the BGA component and passing each one of the plurality of electrical wires through the wire guide. The preceding subject matter of this paragraph characterizes example 19 of the present disclosure, wherein example 19 also includes the subject matter according to example 18, above.

Fixing together the plurality of electrical wires comprises electrically coupling an electrically-conductive bridge to the plurality of electrical wires. The preceding subject matter of this paragraph characterizes example 20 of the present disclosure, wherein example 20 also includes the subject matter according to any of examples 18 or 19, above.

The described features, structures, advantages, and/or characteristics of the subject matter of the present disclosure may be combined in any suitable manner in one or more examples and/or implementations. In the following description, numerous specific details are provided to impart a thorough understanding of examples of the subject matter of the present disclosure. One skilled in the relevant art will recognize that the subject matter of the present disclosure may be practiced without one or more of the specific features, details, components, materials, and/or methods of a particular example or implementation. In other instances, additional features and advantages may be recognized in certain examples and/or implementations that may not be present in all examples or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific examples that are illustrated in the appended drawings. Understanding that these drawings, which are not necessarily drawn to scale, depict only certain examples of the subject matter and are not therefore to be considered to be limiting of its scope, the subject matter will be described and explained with additional specificity and detail through the use of the drawings, in which.

DETAILED DESCRIPTION

Reference throughout this specification to "one example," "an example," or similar language means that a particular feature, structure, or characteristic described in connection with the example is included in at least one example of the present disclosure. Appearances of the phrases "in one example," "in an example," and similar language throughout this specification may, but do not necessarily, all refer to the same example. Similarly, the use of the term "implementation" means an implementation having a particular feature, structure, or characteristic described in connection with one or more examples of the present disclosure, however, absent an express correlation to indicate otherwise, an implementation may be associated with one or more examples.

Disclosed herein is a method of directly attaching electrical wires (e.g., coaxial wires) to the ball-grid array (BGA) of an electrical device (e.g., image sensor), and associated apparatuses formed thereby. As used herein, an electrical device that has a BGA is termed a BGA component. In certain examples, the electrical wires are attached to the solder balls of the BGA component without a wire guide. Such examples promote a more simplistic, streamlined, and cost-effective configuration. However, under certain circumstances, directly attaching the electrical wires to the solder balls of the BGA can be difficult to accomplish due to the size of the wires and the minimal clearance between the solder balls of the BGA component. Moreover, directly attaching the solder balls of the BGA component to the electrical wires without a wire guide might not provide the necessary strength and stability required under certain circumstances. Therefore, in some examples, the method utilizes a wire guide to help strengthen and provide electrical isolation for the electrical connection between the BGA and the electrical wires. The wire guide is small, streamlined, and configured to guide the electrical wires to the solder balls of the BGA component. Additionally, the wire guide is configured to help prevent solder joints, between the electrical wires and respective solder balls of the BGA component, from flowing into each other, thus helping to prevent short circuits. The wire guide is also configured to structurally support the electrical wires and the BGA component, which helps promote a robust attachment between the electrical wires and the BGA component, without a printed circuit board. Furthermore, the wire guide helps to properly position the wires relative to each other such that proper alignment with the solder balls of the BGA is promoted.

Figure 1:
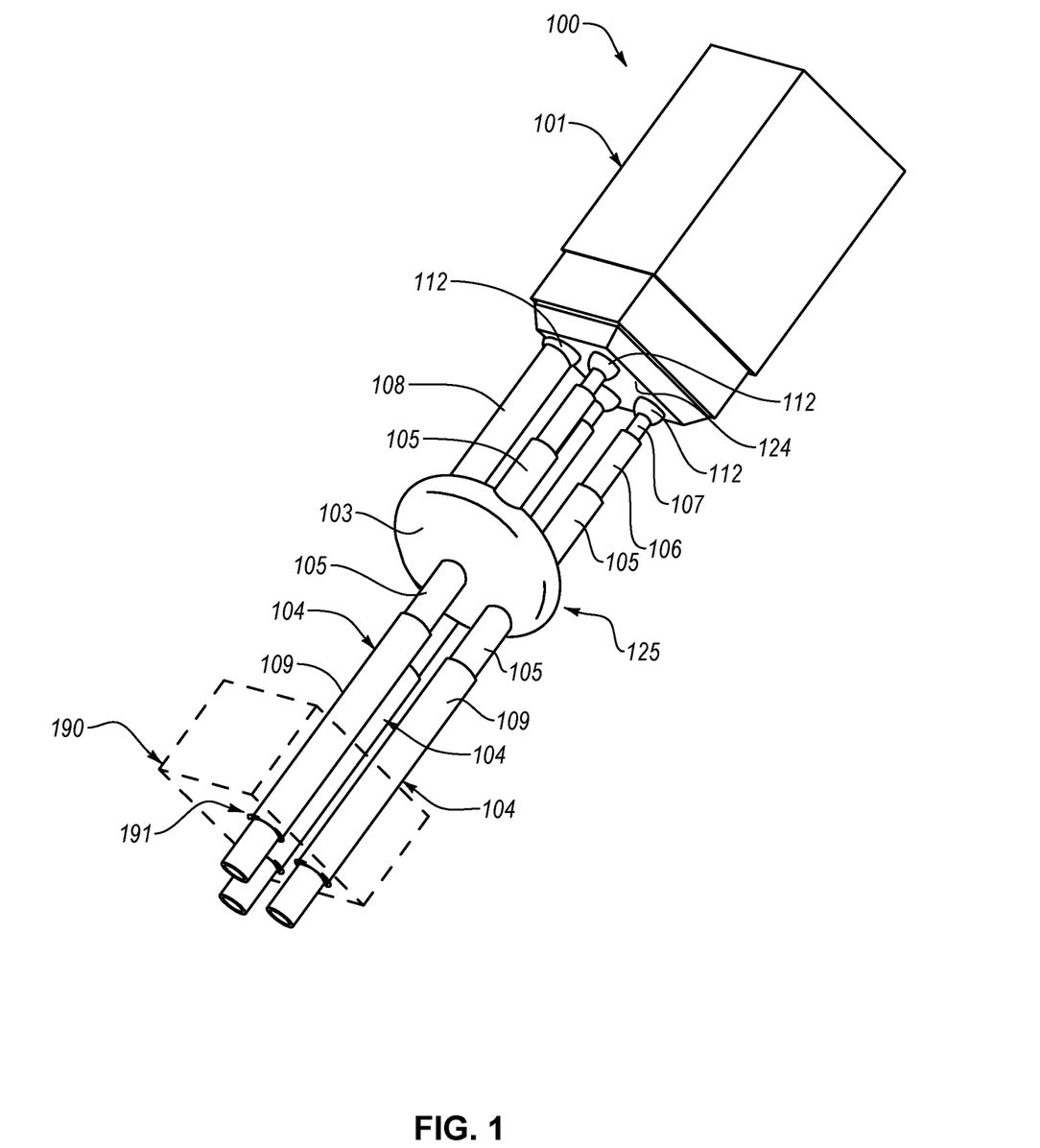
FIG. 1 is a schematic, perspective view of an electrical device, according to one or more examples of the present disclosure.
Figure 2:
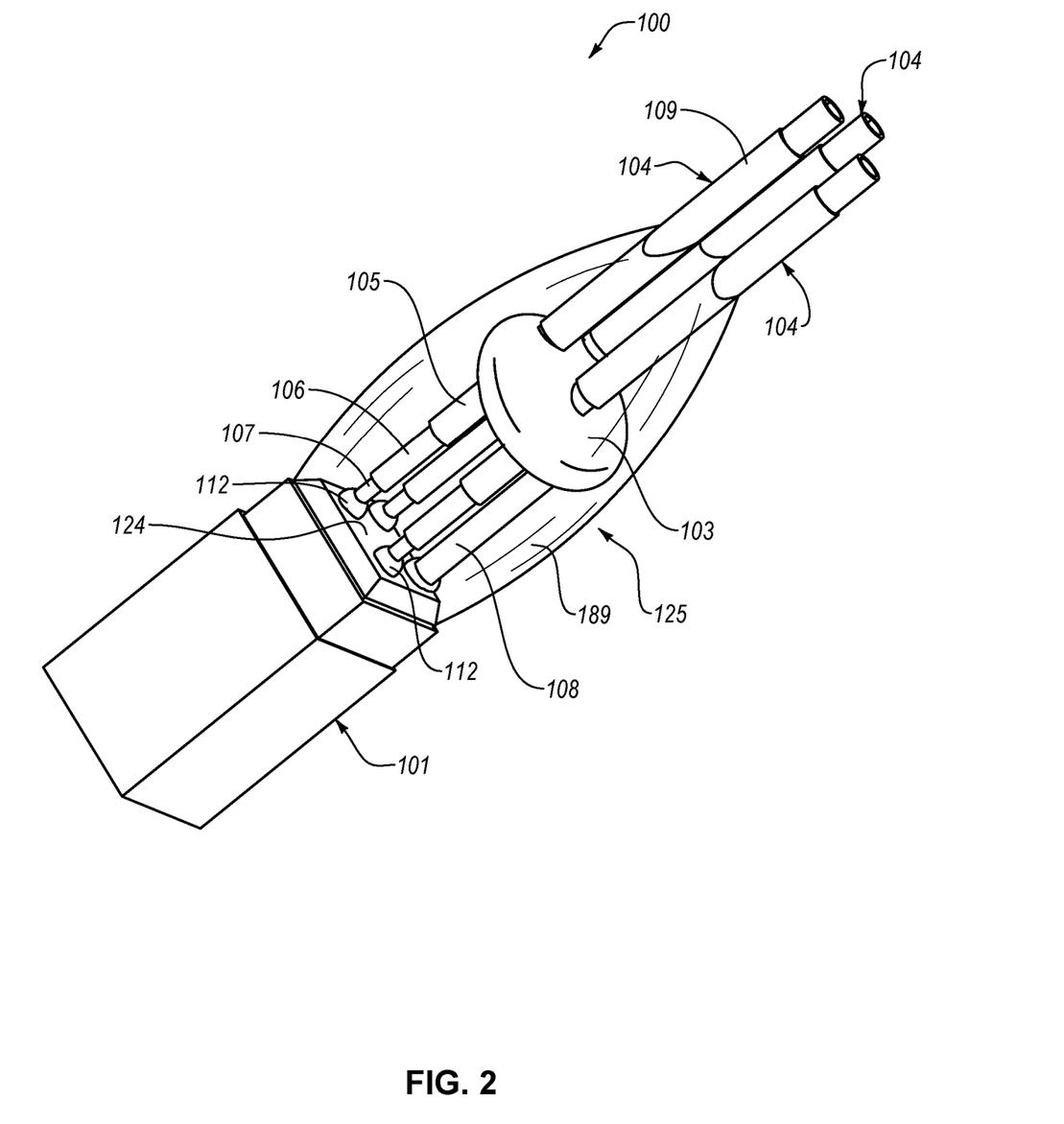
FIG. 2 is a schematic, perspective view of an electrical device, according to one or more examples of the present disclosure.

Referring to FIGS. 1 and 2, and according to some examples, an electrical device 100, with electrical wires attached directly to a BGA component and without a wire guide, is shown. The electrical device 100 includes a BGA component 101, which can be any of various electrical components having a BGA. In certain examples, the BGA component 101 includes signal processing circuitry and a BGA. According to some examples, the signal processing circuitry enables signal-processing, data-capturing, and/or image-capturing capabilities of the BGA component 101. Accordingly, in certain examples, the BGA component 101 is not a passive electrical component, but rather is an electrically powered active electrical component. The BGA has a plurality of solder balls, such as solder balls 112. The solder balls 112 of the BGA are arranged on a component mounting surface 124 of the data-processing device. As used herein, each one of the solder balls can be any of various soldier deposits or reflowable surface mount electrical connections. Moreover, a solder ball need not necessarily have the shape of a ball or sphere to be considered a solder ball (e.g., solder ball can have a semi-spherical shape, a mound shape, a blob shape, or the like). According to some examples, the electrical device 100 is an endoscope and the BGA component 101 is an image sensor (e.g., a camera or an ultrasound sensor) at an exploratory end of the endoscope. Although the BGA component 101 can be a camera in some examples, in other examples, the data-processing device can be any of various sensors, scanners, and the like.

Figure 9:
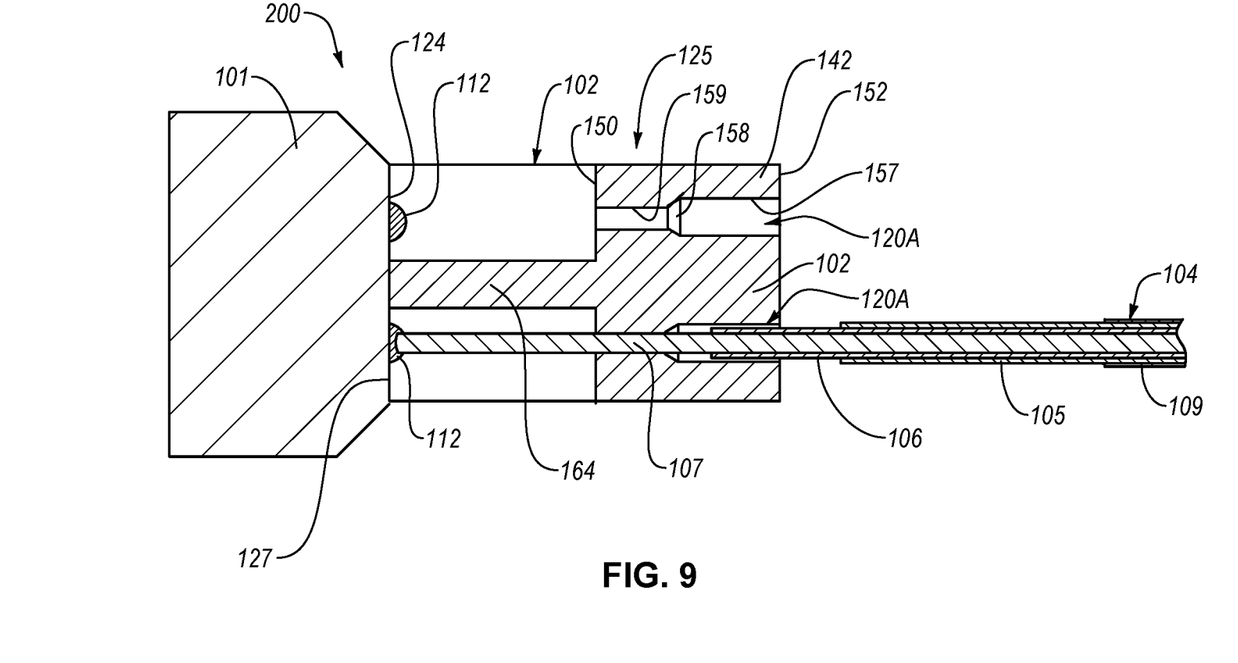
FIG. 9 is a schematic, cross-sectional, side elevation view of the electrical device of FIG. 8, taken along the line 9-9 of FIG. 8, according to one or more examples of the present disclosure.
Figure 10:
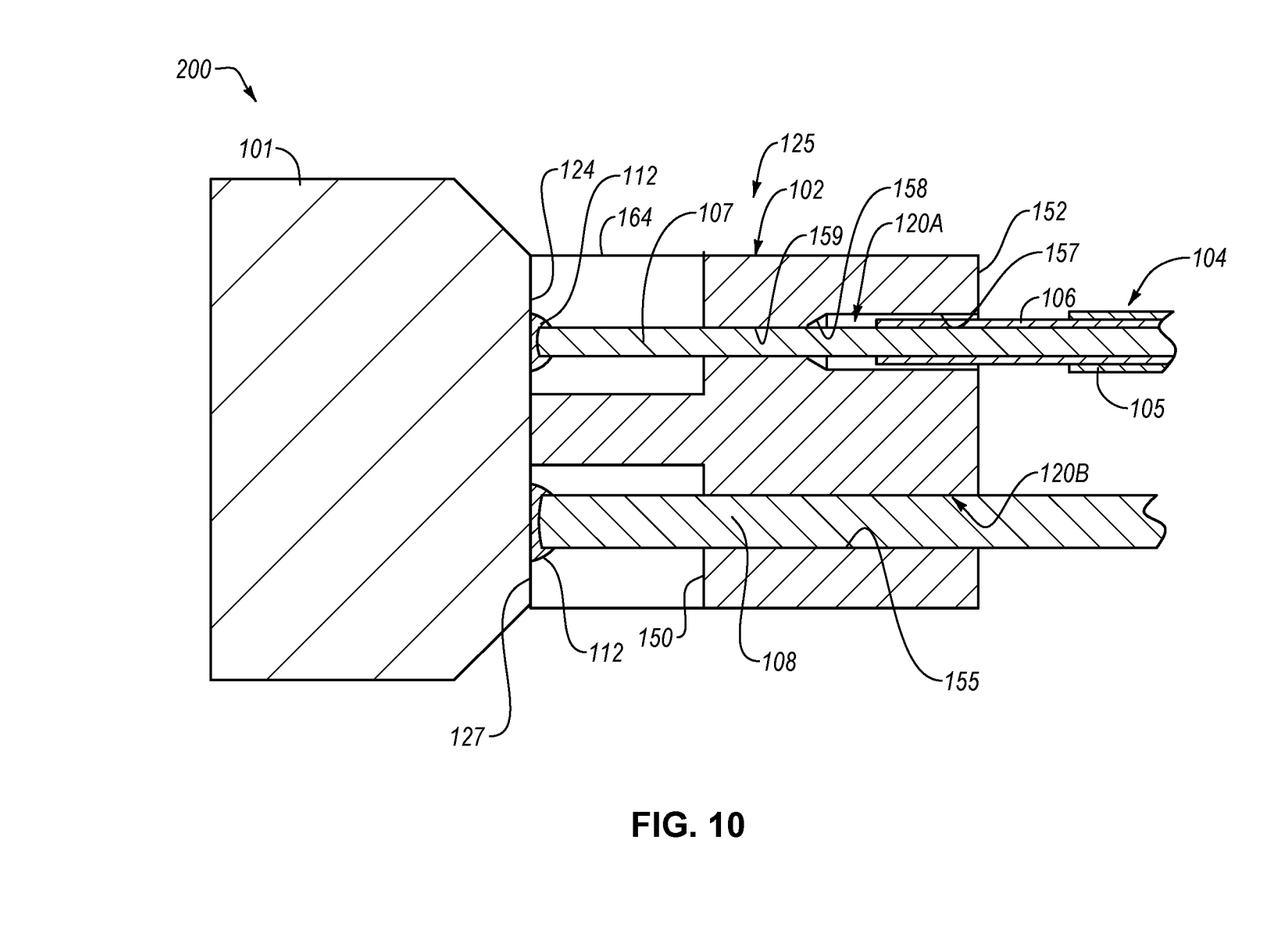
FIG. 10 is a schematic, cross-sectional, side elevation view of the electrical device of FIG. 8, taken along the line 10-10 of FIG. 8, according to one or more examples of the present disclosure.

The BGA component 101 is electrically coupled directly to electrical wires. More specifically, each one of the solder balls 112 of the BGA of the BGA component 101 is electrically coupled to a corresponding one of multiple electrical wires to provide at least one of power to, data to, data from, or a grounding function for the BGA component 101. As used herein, in preferred examples, electrical wires can be coaxial wires or wire slugs. When electrically coupled to the BGA component 101, depending on which solder ball 112 of the BGA the wires are electrically coupled, the electrical wires transmit power, transmit data, or provide a grounding circuit. In the illustrated example of FIGS. 1 and 2, the electrical wires include coaxial wires 104 (e.g., three coaxial wires 104) and a wire slug 108. Referring to FIGS. 9 and 10, each one of the coaxial wires 104 includes multiple coaxial layers, such as a center conductor 107, a dielectric layer 106, a ground layer 105, and a shield layer 109. Although the wires herein are illustrated as coaxial wires 104 with multiple coaxial layers, it is recognized that in some examples, the wires are not coaxial wires, but can be other types of wires.

According to FIGS. 1 and 2, the center conductor 107 of each one of the coaxial wires 104 is positioned on and electrically coupled directly to a corresponding one of the solder balls 112. Similarly, the wire slug 108 is positioned on and electrically coupled directly to a corresponding one of the solder balls 112 associated with a grounding circuit of the BGA component 101. After being electrically coupled, the coaxial wires 104 and the wire slug 108 extend perpendicularly relative to the component mounting surface 124, such that a central axis of the coaxial wires 104 is perpendicular to the component mounting surface 124. Electrically coupling the center conductors 107 and the wire slug 108 to the solder balls includes reflowing the solder balls with the center conductors 107 and the wires slug 108 in place against the solder balls, which, when allowed to harden, establishes a permanent electrical and structural connection between the BGA component 101 and the center conductors 107 and between the BGA component 101 and the wire slug 108. The solder balls 112 of the BGA are spaced apart from each other such that the center conductors 107 of the coaxial wires 104 and the wire slug 108 are spaced apart and electrically isolated from each other.

To facilitate proper electrical connection between the BGA component 101 and the electrical wires, portions of layers of the coaxial wires 104 are stripped to expose, in a staggered manner along an axis of the coaxial wires 104, the center conductor 107, the dielectric layer 106, and the ground layer 105. For example, portions of the shield layer 109, the ground layer 105, and the dielectric layer 106 are removed so that a portion of the center conductor 107, the dielectric layer 106, and the ground layer 105 is exposed. The center conductor 107 is the innermost layer of the coaxial wire 104, the shield layer 109 is the outermost layer of the coaxial wire 104, the dielectric layer 106 is interposed between the center conductor 107 and the ground layer 105, and the ground layer 105 is interposed between the dielectric layer 106 and the shield layer 109. After three of the solder balls 112 are soldered directly to the center conductors 107 of the three coaxial wires 104, a fourth one of the solder balls 112 is soldered directly to the wire slug 108. Accordingly, the fourth one of the solder balls 112, in this example, is a grounding solder ball.

The wire slug 108 helps to electrically connect the grounding solder ball to the ground layer 105 of all the coaxial wires 104. For example, as shown in FIGS. 1 and 2, the electrical device 100 further includes a wire fixation element 125. The wire fixation element 125 is configured to fix the electrical wires relative to each other, so that the electrical wires do not move relative to each other, which helps to stiffen and strengthen the electrical coupling between the electrical wires and the BGA component 101. The electrical wires at least partially pass through the wire fixation element 125 so that the wire fixation element 125 entirely circumferentially surrounds a portion of each one of the electrical wires. Moreover, a portion of the wire fixation element 125 is interposed between each one of the electrical wires.

According to some examples, as shown in FIGS. 1 and 2, the wire fixation element 125 is an electrically-conductive bridge 103, made of an electrically conductive material. The electrically-conductive bridge 103 contacts and at least partially envelops a portion of the wire slug 108 and a portion of the ground layer 105 of all the coaxial wires 104. In this manner, the wire slug 108 and the ground layers 105 of the coaxial wires 104 are electrically connected. The application and size of the electrically-conductive bridge 103 is selected so that no portion of the electrically-conductive bridge 103 contacts the center conductor 107 of any one of the coaxial wires 104. In certain examples, the electrically-conductive bridge 103 is a solder blob made of solder material. However, in other examples, the electrically-conductive bridge 103 is made from another type of electrically conductive material, such as a conductive epoxy, metallic material, or the like.

In some instances, as shown in FIG. 2, to help promote strength and rigidity, the wire fixation element 125 can further include an electrically non-conductive material 189, which can be added to the electrical device 100 shown in FIG. 1. The non-conductive material 189, which can be an epoxy, an adhesive, a glue, etc., is located in an area extending from the component mounting surface 124 to beyond the electrically-conductive bridge 103. The non-conductive material 189 surrounds and envelops an entirety of the electrical device 100 within the area. In other words, in some examples, the non-conductive material 189 surrounds and envelops at least a portion of the component mounting surface 124, the electrically-conductive bridge 103, the portion of the electrical wires between the component mounting surface 124 and the electrically-conductive bridge 103, and at least a portion of the electrical wires extending out of the electrically-conductive bridge 103 away from the component mounting surface 124. In certain examples, the non-conductive material 189 surrounds and envelops at least a portion of the component mounting surface 124, an entirety of the electrically-conductive bridge 103, an entirety of the wire slug 108, an entirety of the coaxial wires 104 between the component mounting surface 124 and the electrically-conductive bridge 103, and at least a portion of the coaxial wires 104 extending out of the electrically-conductive bridge 103 away from the component mounting surface 124 Accordingly, the non-conductive material 189 abuts the component mounting surface 124 such that the non-conductive material 189 defines a structurally rigid member extending from the BGA component 101 to the coaxial wires 104. In this manner, the non-conductive material is configured to increase robustness of the electrical device 100 by stiffening the device and the electrical coupling between the BGA component 101 and the coaxial wires 104. In other examples, the non-conductive material 189 can be substituted with a crimp, plate, or another stiffening material to improve the robustness of the electrical device 100, such as for handling and durability.

As further shown in FIG. 1, in some examples, a fixture 190 can be used to hold the coaxial wires 104 in place while the coaxial wires 104 are soldered to the solder balls 112 of the BGA component 101. The fixture 190 can include holes 191 through which the coaxial wires 104 pass through and which support the coaxial wires 104 in place. The holes 191 are arranged to complement the arrangement of the solder balls 112 of the BGA component, such that when the coaxial wires 104 pass through and are supported by the fixture 190, the coaxial wires 104 are aligned with the solder balls 112 to help facilitate ease in soldering the coaxial wires 104 directly to the solder balls 112. After the coaxial wires 104 are soldered to the solder balls 112, the fixture 190 is removed.

Figure 8:
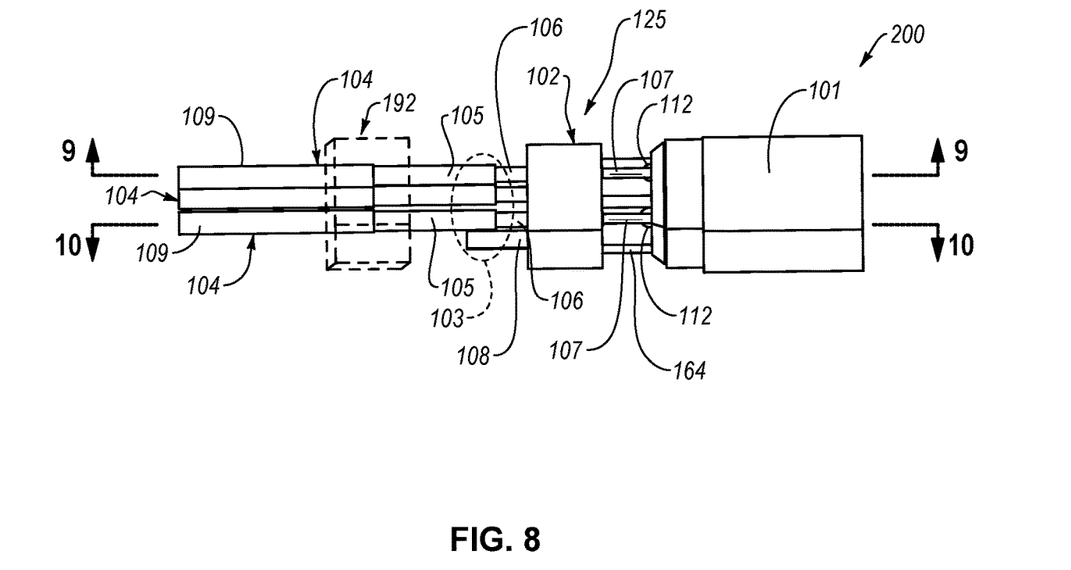
FIG. 8 is a schematic, perspective view of an electrical device, according to one or more examples of the present disclosure.

To help facilitate coupling the coaxial wires 104 and the wire slug 108 directly to the BGA component 101, in some examples, as shown in FIGS. 8-10, the wire fixation element 125 of an electrical device 200 is a wire guide 102. The electrical device 200 is similar to the electrical device 100, with like numbers referring to like elements. For example, the electrical device 200 can be an endoscope and the BGA component 101 can be a camera. The wire guide 102 provides location guidance and self-fixturing of the coaxial wires 104 and the wire slug 108 relative to each other. Moreover, the wire guide 102 structurally supports in place at least the center conductors 107 and the dielectric layer 106 of the coaxial wires 104, and the wire slug 108, which promotes a reliable and robust attachment to the BGA component 101.

Referring to FIGS. 4-7, the wire guide 102 includes a body 142 and a plurality of wire channels (e.g., first wire channels 120A and a second wire channel 120B). In some examples, an outermost periphery of the body 142, which defines an outermost periphery of the wire guide 102, as defined relative to a plane parallel to the component mounting surface 124, does not extend beyond (e.g., is not larger than) an outermost periphery of the BGA component 101, as defined relative to the same plane, such that the wire guide 102 is at least as streamlined as the BGA component 101. In some examples, the outermost peripheral shape and size of the body 142 is the same as that of the BGA component 101. Although the wire guide 102 can include any number of wire channels, in the illustrated examples, the wire guide 102 includes four wire channels. For example, as illustrated, the wire guide 102 includes three first wire channels 120A and one second wire channel 120B (e.g., a slug channel). Moreover, although the wire channels can be arranged relative to each other in any of various arrangements, in the illustrated example, the plurality of wire channels are located so that each one of the wire channels is located in a respective one of four quadrants of the wire guide 102.

The body 142 of the wire guide 102 is made of an electrically non-conductive material, such as a polymeric material. Each one of the first wire channels 120A is configured to house or receive a coaxial wire 104 (e.g., coaxial cable) and the second wire channel 120B is configured to house or receive a wire slug 108. Moreover, the plurality of channels of the wire guide 102 are circumferentially closed and spaced apart from each other. Accordingly, when retained by the plurality of channels (e.g., the first wire channels 120A and the second wire channel 120B), the plurality of center conductors and the wire slug 108 are electrically isolated from each other by the body 142 of the wire guide 102. The first wire channels 120A and the second wire channel 120B of the wire guide 102 extend from a front surface 150 of the body 142 to a rear surface 152 of the body 142. Accordingly, the first wire channels 120A and the second wire channel 120B extend entirely through the body 142 between the front surface 150 and the rear surface 152. Accordingly, the coaxial wires 104 and the wire slug 108 are accessible at both the front surface 150 and the rear surface 152.

Referring to FIGS. 9 and 10, some of the wire channels, such as the first wire channels 120A, have a converging section 158 such that the wire channels each have a first section 157, having a first diameter, and a second section 159, having a second diameter. The first section 157 extends from the rear surface 152, the second section 159 extends from the front surface 150, and the converging section 158 is between the first section 157 and the second section 159, and converges from the first section 157 to the second section 159. The first diameter is substantially equal to (e.g., slightly more than) a diameter of the dielectric layer 106 and the second diameter is substantially equal to (e.g., slightly more than) a diameter of the center conductor 107. Accordingly, when inserted into a corresponding one of the wire channels, the dielectric layer 106 is seated within first section 157 and center conductor 107 is seated within second section 159. In some examples, the first diameter and the second diameter are such that the dielectric layer 106 forms a transition fit with the first section 157 and/or the center conductor 107 forms a transition fit with the second section 159. As defined herein, a transition fit is a fit between a clearance fit and an interference fit, when accurate alignment is preferred and mating parts join with precision. In certain examples, a transition fit can also be referred to as a slip fit or a push fit. Although less preferrable, in some examples, instead of a transition fit, the wire channels are configured to provide a clearance fit or an interference fit with the wires. As shown in FIG. 10, in some examples, a diameter of the second wire channel 120B is larger than the first diameter of the first section 157 and the second diameter of the second section 159 to accommodate the diameter of the wire slug 108, which in some examples is larger than the diameters of the center conductor 107 and the dielectric layer 106 of the coaxial wires 104. Additionally, the slug channel 155 has a constant diameter to accommodate the constant diameter of the wire slug 108.

Referring to FIGS. 9 and 10, the wire guide 102 abuts the component mounting surface 124 of the BGA component 101, which strengthens the electrical coupling between the BGA component 101 and the plurality of center conductors 107, and the BGA component 101 and the wire slug 108, by providing a direct mechanical coupling between the wire guide 102 and the BGA component 101. The wire guide 102 further includes at least one wall 164 extending from the rear surface 152 of the body 142, in a direction perpendicular to the rear surface 152 of the body 142. In the illustrated examples, the at least one wall 164 includes two walls, which are perpendicular to each other and intersect at a midpoint of the walls such that four distinct open channels are separated by the walls. Accordingly, in such examples, the at least one wall 164 defines a cruciform. Each one of the open channels is open (e.g., aligned with) a corresponding one of the first wire channels 120 and the second wire channel 120B of the 142. A distal end surface 127 of the at least one wall 164, which is located away from the rear surface 152 and has a substantially '+' cross-sectional shape in some examples, contacts the component mounting surface 124 of the BGA component 101. This configuration enables the four distinct open channels to receive a corresponding one of the plurality of center conductors 107 and the wire slug 108 and allows isolated access for soldering. In other words, the open channels defined by the at least one wall 164 prevent solder from the solder balls 112 from flowing together during soldering of the electrical wires to the solder balls 112, which prevents possible short circuiting at the BGA of the BGA component 101. Accordingly, the wire guide 102 is configured to separate the solder balls 112 of the BGA of the BGA component 101 to prevent solder flow from one solder ball of the BGA to another.

Figure 3:
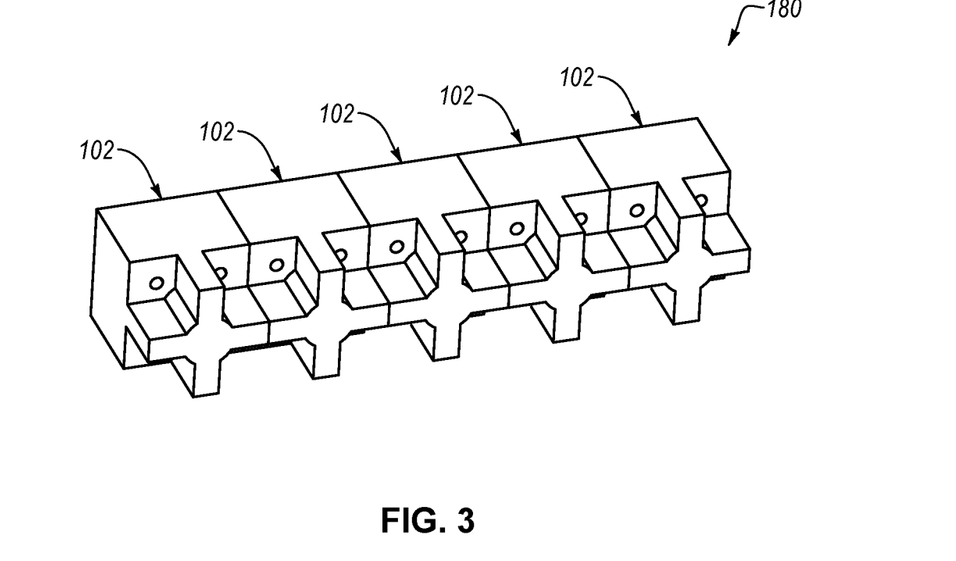
FIG. 3 is a schematic, perspective view of a ganged unit of wire guides, according to one or more examples of the present disclosure.
Figure 4:
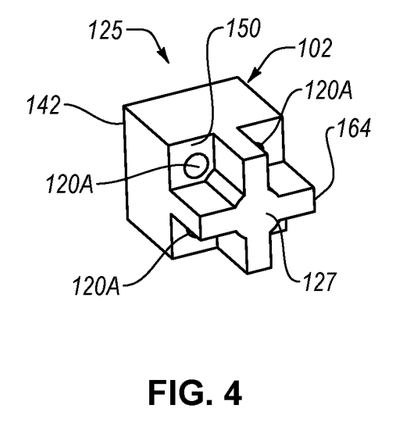
FIG. 4 is a schematic, perspective view of an electrical device, from a front of the electrical device, according to one or more examples of the present disclosure.
Figure 5:
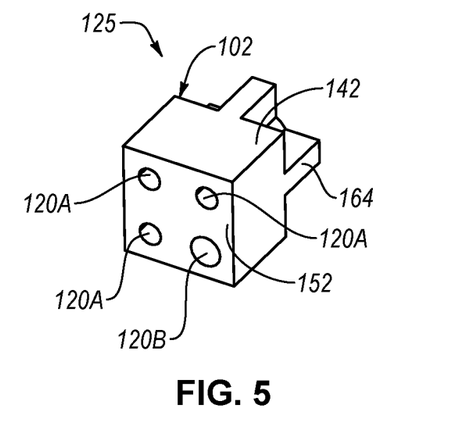
FIG. 5 is a schematic, perspective view of the electrical device of FIG. 4, from a rear of the electrical device, according to one or more examples of the present disclosure.
Figure 6:
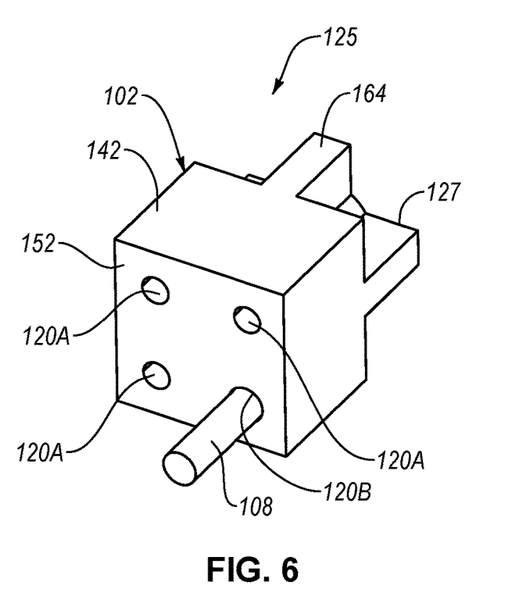
FIG. 6 is a schematic, perspective view of the electrical device of FIG. 4 and a wire slug, from a rear of the electrical device, according to one or more examples of the present disclosure.
Figure 7:
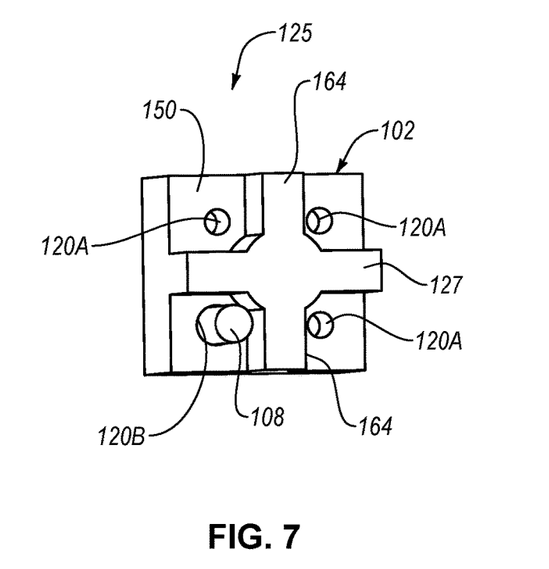
FIG. 7 is a schematic, perspective view of the electrical device of FIG. 4 and a wire slug, from a front of the electrical device, according to one or more examples of the present disclosure.

The wire guide 102 can be manufactured in any of various ways. In some examples, the wire guide 102 is manufactured to have a one-piece monolithic and seamless construction (e.g., the body 142 and the at least one wall 164 are co-formed to have a one-piece monolithic and seamless construction). In one example, the wire guide 102 is injection molded one piece at a time. However, because the wire guides 102 can be smaller than 1 square-millimeter (mm²) in some examples, molding multiple wire guides 102 can be helpful for handling. For example, referring to FIG. 3, a plurality of wire guides 102 are molded together as a ganged unit 180. After forming the ganged unit 180, the wire guides 102 of the ganged unit 180 are separated by being broken or cut apart at thin break-away interfaces between adjacent ones of the wire guides 102 of the ganged unit 180. The larger shot size associated with the ganged unit 180, compared to an individual wire guide 102, promotes an easier and more efficient injection molding process.

In some examples, the wire guide 102 can be glued to the component mounting surface 124 of the BGA component 101 prior to soldering the coaxial wires 104 and the wire slug 108 to the BGA. Alternatively, the wire guide 102 can be fixture-held against the component mounting surface 124 prior to and during the soldering process.

Referring to FIG. 8, according to some examples, the electrical device 200 further includes an electrically-conductive bridge 103, similar to the electrically-conductive bridge 103 of the electrical device 100 of FIG. 1. In such examples, the electrically-conductive bridge 103 is disposed on the terminating end of the wire slug 108 and on the ground layer 105 of the plurality of coaxial wires 104. Accordingly, the electrically-conductive bridge 103 is used to electrically couple together the wire slug 108 and the ground layers 105 of the plurality of coaxial wires 104.

As further shown in FIG. 8, in some examples, a fixture 192 can be used to hold the coaxial wires 104 in place while the wire guide 102 is formed about the coaxial wires 104. In previous examples, the wire guide 102 is pre-formed and the coaxial wires 104 are passed through the pre-formed wire guide 102 before being soldered to the solder balls 112. However, in other examples, the wire guide 102 can be formed around the coaxial wires 104, and into abutment with the component mounting surface 124, while the coaxial wires 104 are held in place by the fixture 192. The coaxial wires 104 can be soldered to the solder balls 112 before the wire guide 102 is formed (because the fixture 192 holds the coaxial wires 104 in a proper position for soldering) or the coaxial wires 104 can be soldered to the solder balls 112 after the wire guide 102 is formed about the coaxial wires 104. In examples where the wire guide 102 is formed about coaxial wires 104, the wire guide 102 can be made from any of various materials, such as epoxy, hot melt glue, plastic, and the like. After the wire guide 102 is formed (and, in some examples, after the coaxial wires 104 are soldered to the solder balls 112), the fixture 192 is removed.

In certain examples, the fixture 192 is made of any of various materials, such as Teflon, and includes holes through which the coaxial wires 104 pass through and which support the coaxial wires 104 in place. Similar to the fixture 190, the holes of the fixture 192 are arranged to complement the arrangement of the solder balls 112 of the BGA component, such that when the coaxial wires 104 pass through and are supported by the fixture 192, the coaxial wires 104 are aligned with the solder balls 112 to ensure the coaxial wires 104 are properly positioned when the wire guide 102 is formed.

Figure 11:
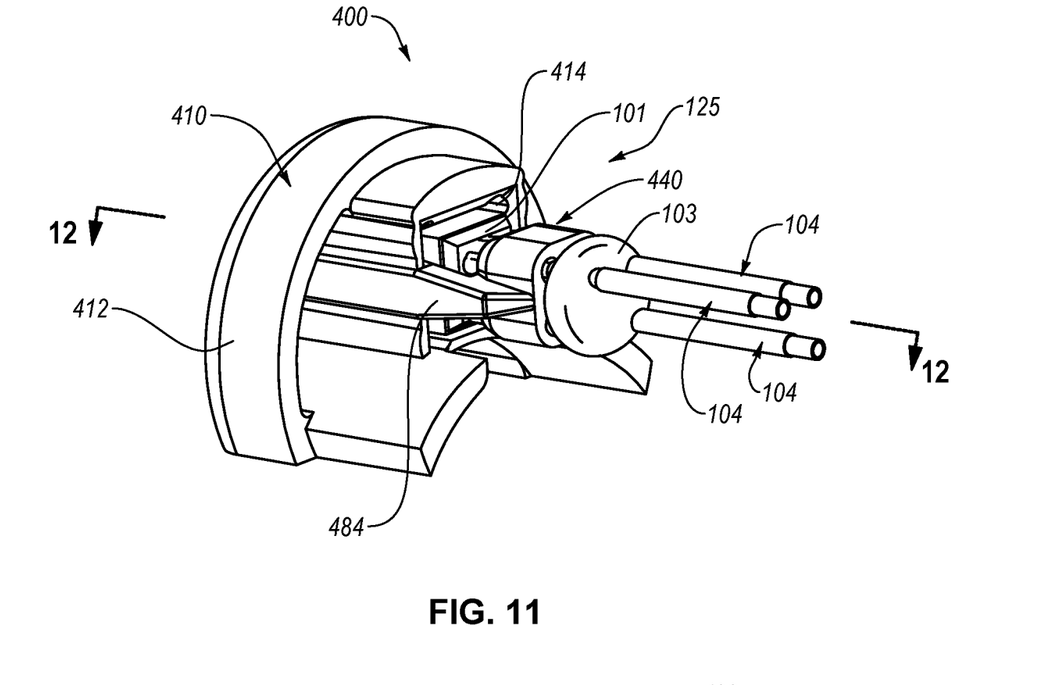
FIG. 11 is a schematic, perspective view of an electrical device, according to one or more examples of the present disclosure.
Figure 12:
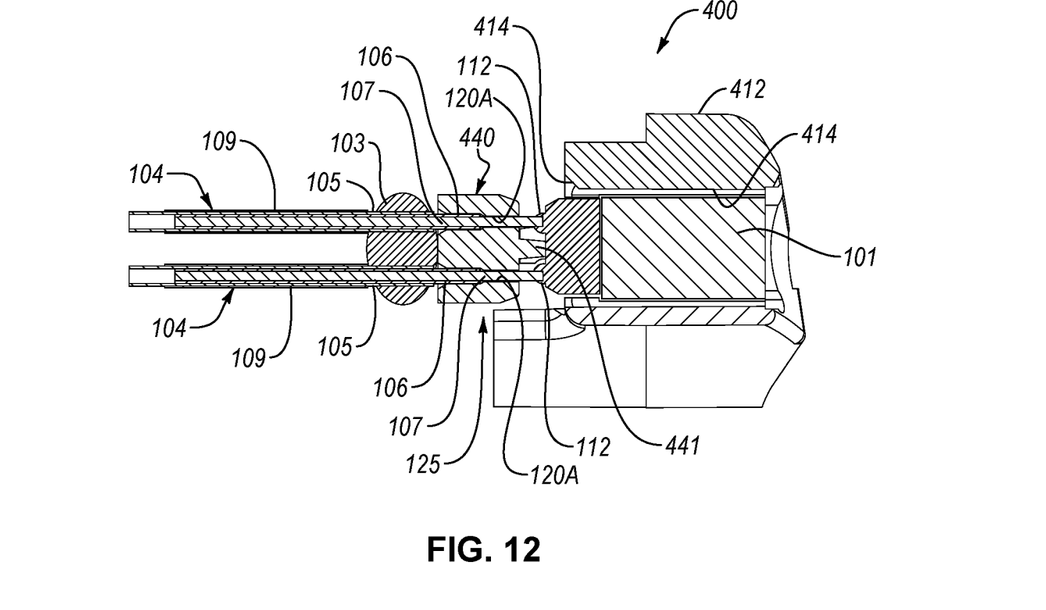
FIG. 12 is a schematic, cross-sectional, side elevation view of the electrical device of FIG. 11, taken along the line 12-12 of FIG. 11, according to one or more examples of the present disclosure.

Referring to FIGS. 11 and 12, according to some examples, an electrical device 400 is an endoscope and the BGA component 101 is a camera. The electrical device 400 of FIGS. 11 and 12 includes features similar to the electrical device 200 of FIGS. 8-10. Additionally, the electrical device 400 of FIGS. 11 and 12 includes a tip assembly 410. To help facilitate coupling the coaxial wires 104 and the wire slug 108 directly to the BGA component 101, the electrical device 400 includes a wire fixation element 125, which is a wire guide 440 in the illustrated example. The tip assembly 410 includes a tip housing 412 and the wire guide 440. The tip housing 412 and the wire guide 440 are coupled together, such as co-molded together to form a one-piece monolithic construction. Such a configuration enables the tip housing 412 to act as a handle while the wire slug 108 and plurality of coaxial wires 104 are inserted (e.g., transition fit) into the body of the wire guide 440. Additionally, the monolithic construction of the tip housing 412 and the wire guide 440 helps reduce part count.

The tip housing 412 is configured to house the BGA component 101. To this end, the tip housing 412 includes a receptacle 414 (e.g., channel) that has a cross-sectional size and shape that complements that of the BGA component 101 such that the BGA component 101 is received in and retained by the receptacle 414 via a slip fit, a transition fit, a press fit, or the like. Furthermore, the tip housing 412 defines a leading end surface of the electrical device 400.

The wire guide 440, which includes features similar to the wire guide 102 described above, is fixed to the tip housing 412 such that the wire guide 440 does not move relative to the tip housing 412. In one example, the wire guide 440 is fixed to the tip housing 412, via integrated wings 484 (e.g., co-formed with the wire guide 440 and the tip housing 412), and positioned such that the wire guide 440 is located at a trailing end of the receptacle 414. In this manner, the BGA component 101 can be slid into the receptacle 414 up to and abutting a surface of the wire guide 440, defined by at least one wall 441 (e.g., two walls forming a cruciform shape) of the wire guide 440. The wings 484 extend between, and couple together, the tip housing 412 and the wire guide 440.

Similar to the electrical device 200 of FIGS. 8-10, the coaxial wires 104 of the electrical device 400 are stripped down so that the center conductors 107 can be passed through wire channels of the wire guide 440 and soldered to the BGA of the BGA component 101. Similarly, a wire slug is passed through a corresponding one of the channels of the wire guide 440 and soldered to the BGA. As with the wire guide 102, the wire guide 440 separates the coaxial wires 104 and the wire slug and prevents short circuiting from running solder and exposed center conductors 107. In some examples, the coaxial wires 104 and the wire slug are grounded together by an electrically-conductive bridge 103.

Referring to FIG. 12, in an axial direction, parallel with the coaxial wires 104, towards the BGA component 101, the shield layers 109 of the coaxial wires 104 terminate at or before the electrically-conductive bridge 103. The ground layers 105 of the coaxial wires 104 are exposed after the shield layers 109 and are least partially enveloped by the electrically-conductive bridge 103. The ground layers 105 terminate in or after the electrically-conductive bridge 103. An exposed portion of the dielectric layers 106 extend into a corresponding one of the first wire channels 120A of the wire guide 102. The dielectric layers 106 terminate inside the first wire channels 120A and an exposed portion of the center conductors 107 continue through the first wire channels 120A. The center conductors 107 extend from the first wire channels 120A where they are soldered to corresponding ones of the solder balls 112 of the BGA of the BGA component 101, which is secured within the receptacle 414 of the tip housing 412.

Figure 13:
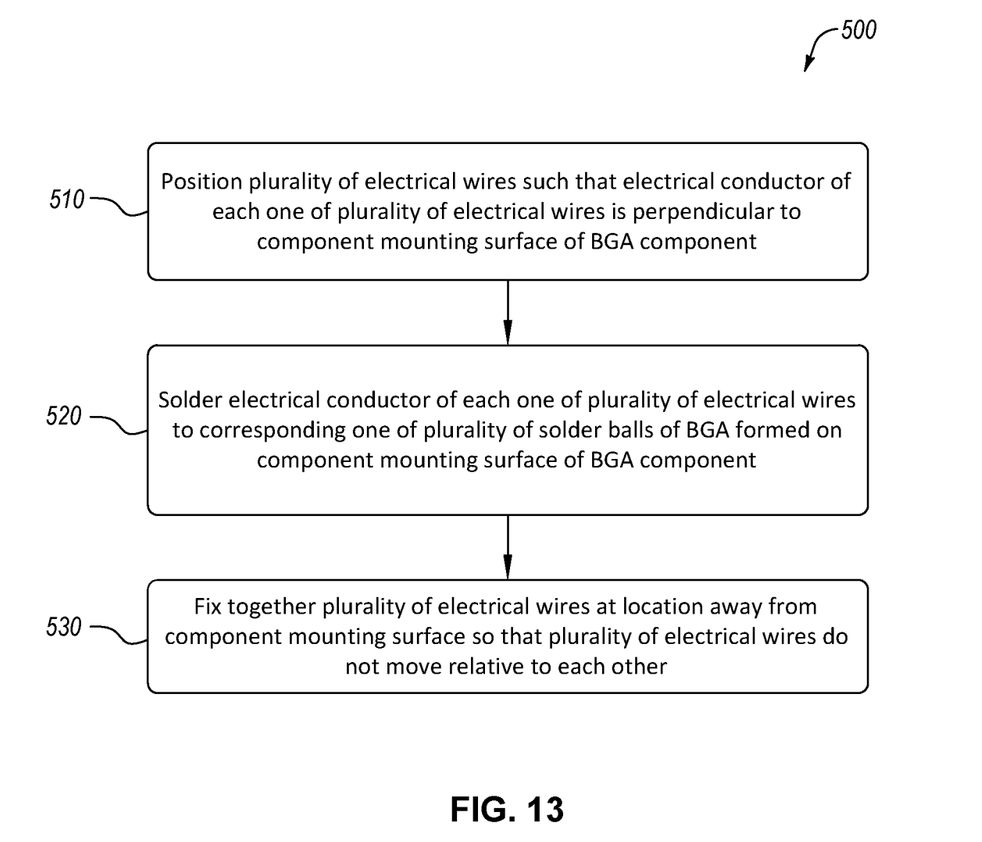
FIG. 13 is a schematic flow chart of a method of making an electrical device, according to one or more examples of the present disclosure.

Referring to FIG. 13, according to some examples, a method 500 of making an electrical device, such as one of the electrical devices disclosed herein, includes (block 510) positioning a plurality of electrical wires such that an electrical conductor of each one of the plurality of electrical wires is perpendicular to a component mounting surface of a BGA component. The method 500 also includes (block 520) soldering the electrical conductor of each one of the plurality of electrical wires, when positioned perpendicular to the component mounting surface of the BGA component, to a corresponding one of a plurality of solder balls of a BGA formed on the component mounting surface of the BGA component. The method 500 additionally includes (block 530) fixing together the plurality of electrical wires at a location away from the component mounting surface so that the plurality of electrical wires do not move relative to each other.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two." Moreover, unless otherwise noted, as defined herein a plurality of particular features does not necessarily mean every particular feature of an entire set or class of the particular features.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The schematic flow chart diagrams included herein are generally set forth as logical flow chart diagrams. As such, the depicted order and labeled steps are indicative of one example of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described examples are to be considered in all respects only as illustrative and not restrictive. All changes which come within the meaning and range of equivalency of the claims are to be embraced within their scope.

What is claimed is:

1. An electrical device comprising:
a ball grid array (BGA) component, comprising signal processing circuitry, a component mounting surface, and a BGA, wherein the BGA comprises solder balls that are spaced apart from each other on the component mounting surface;
a plurality of electrical wires, each electrically coupled directly to a corresponding one of the solder balls of the BGA component; and
a wire fixation element, through which the plurality of electrical wires at least partially pass through, wherein the wire fixation element is coupled to the plurality of electrical wires and configured to fix the electrical wires relative to each other so that the electrical wires do not move relative to each other.

2. The electrical device according to claim 1, wherein the plurality of electrical wires extend perpendicularly relative to the component mounting surface of the BGA component.

3. The electrical device according to claim 2, wherein:
the plurality of electrical wires comprise coaxial wires each comprising a center conductor, a dielectric layer encircling the center conductor, and a ground layer encircling the dielectric layer; and
each one of the coaxial wires passes entirely through the wire fixation element.

4. The electrical device according to claim 3, wherein:
the plurality of electrical wires further comprises a wire slug; and
the wire slug is electrically coupled directly to a grounding one of the solder balls of the BGA component.

5. The electrical device according to claim 4, wherein:
the wire slug only partially passes through the wire fixation element; and
the wire fixation element comprises an electrically-conductive bridge in contact with and electrically coupling together the ground layers of the coaxial wires and the wire slug.

6. The electrical device according to claim 5, wherein the wire fixation element further comprises a non-conductive material that surrounds and envelopes at least a portion of the component mounting surface, an entirety of the wire slug, an entirety of the electrically-conductive bridge, an entirety of the coaxial wires between component mounting surface and the electrically-conductive bridge, and at least a portion of the coaxial wires extending out of the electrically-conductive bridge away from the component mounting surface.

7. The electrical device according to claim 4, wherein:
the wire fixation element comprises a wire guide, which abuts the component mounting surface and comprises a plurality of wire channels;
the plurality of wire channels are spaced apart from each other; and
each one of the coaxial wires and the wire slug passes entirely through a corresponding one of the plurality of wire channels.

8. The electrical device according to claim 7, wherein:
the wire guide comprises a body and at least one electrically insulating wall extending from the body;
the body comprises the plurality of wire channels;
the at least one electrically insulating wall defines open channels isolated from each other by the at least one electrically insulating wall;
the at least one electrically insulating wall abuts the component mounting surface of the BGA component; and
each one of the coaxial wires and the wire slug occupies a corresponding one of the open channels defined by the at least one electrically insulating wall.

9. The electrical device according to claim 7, wherein:
each one of the plurality of wire channels, through which coaxial wires pass, comprises a first section and a second section;
the first section has a diameter substantially equal to a diameter of the dielectric layer so that the dielectric layer forms a transition fit with the first section;
the second section has a diameter substantially equal to a diameter of the center conductor so that the center conductor forms a transition fit with the second section; and
the diameter of the first section is greater than the diameter of the second section.

10. The electrical device according to claim 9, wherein the wire channel, through which the wire slug passes, has a diameter greater than the diameter of the first section.

11. The electrical device according to claim 8, wherein:
the wire fixation element further comprises an electrically-conductive bridge in contact with and electrically coupling together the ground layers of the coaxial wires and the wire slug; and
the wire guide is interposed between the component mounting surface and the electrically-conductive bridge.

12. The electrical device according to claim 11, wherein the electrically-conductive bridge comprises a solder blob.

13. The electrical device according to claim 7, further comprising a tip assembly, comprising a tip housing and the wire guide, wherein:
the tip housing comprises a receptacle that houses the BGA component; and
the tip housing and the wire guide form a one-piece monolithic and seamless construction.

14. The electrical device according to claim 7, wherein an outermost periphery of the wire guide, defined relative to a plane that is parallel to the component mounting surface, is not larger than an outermost periphery of the BGA component, defined relative to the plane.

15. An endoscope comprising:
an image sensor, comprising a component mounting surface and a ball grid array (BGA), having solder balls spaced apart from each other, on the component mounting surface;
a plurality of coaxial wires, each electrically coupled directly to a corresponding one of the solder balls of the image sensor and each extending perpendicularly relative to the component mounting surface of the image sensor; and
a wire fixation element, through which the plurality of coaxial wires entirely pass through, wherein the wire fixation element is coupled to the plurality of coaxial wires and configured to fix the coaxial wires relative to each other so that the coaxial wires do not move relative to each other.

16. The endoscope according to claim 15, wherein an outermost periphery of the wire fixation element, defined relative to a plane that is parallel to the component mounting surface, is not larger than an outermost periphery of the image sensor, defined relative to the plane.

17. The endoscope according to claim 15, wherein:
each one of the coaxial wires comprises a center conductor, a dielectric layer encircling the center conductor, and a ground layer encircling the dielectric layer;
the endoscope further comprises a wire slug electrically coupled directly to a grounding one of the solder balls of the image sensor and extending perpendicularly relative to the component mounting surface of the image sensor; and
the wire fixation element comprises at least one of:
an electrically-conductive bridge in contact with and electrically coupling together the ground layers of the coaxial wires and the wire slug; or
a wire guide, which abuts the component mounting surface and comprises a plurality of channels, wherein the plurality of wire channels are spaced apart from each other, and wherein each one of the coaxial wires and the wire slug passes entirely through a corresponding one of the plurality of wire channels.

18. A method of making an electrical device, the method comprising steps of:
positioning a plurality of electrical wires such that an electrical conductor of each one of the plurality of electrical wires is perpendicular to a component mounting surface of a ball grid array (BGA) component;
soldering the electrical conductor of each one of the plurality of electrical wires, when positioned perpendicular to the component mounting surface of the BGA component, to a corresponding one of a plurality of solder balls of a BGA formed on the component mounting surface of the BGA component; and
fixing together the plurality of electrical wires at a location away from the component mounting surface so that the plurality of electrical wires do not move relative to each other.

19. The method according to claim 18, wherein the step of fixing together the plurality of electrical wires comprises:
abutting a wire guide against the component mounting surface of the BGA component; and
passing each one of the plurality of electrical wires through the wire guide.

20. The method according to claim 18, wherein the step of fixing together the plurality of electrical wires comprises electrically coupling an electrically-conductive bridge to the plurality of electrical wires.

* * * * *